United States Patent [19]

Ellis

[11] Patent Number: 4,674,330

[45] Date of Patent: Jun. 23, 1987

[54] APPARATUS FOR MEASUREMENT OF GRIP AND PINCH STRENGTH

[75] Inventor: Malcolm I. Ellis, Leeds, England

[73] Assignee: MIE Medical Research Limited, Leeds, England

[21] Appl. No.: 838,427

[22] Filed: Mar. 7, 1986

Related U.S. Application Data

[63] Continuation-in-part of Ser. No. 693,178, Jan. 22, 1985, abandoned.

[30] Foreign Application Priority Data

Jan. 24, 1984 [GB] United Kingdom ............... 8401841

[51] Int. Cl.⁴ .............................................. A61B 5/22
[52] U.S. Cl. ..................................................... 73/379
[58] Field of Search ............................ 73/379, 862.65; 128/774

[56] References Cited

U.S. PATENT DOCUMENTS

| | | | |
|---|---|---|---|
| 3,031,152 | 4/1962 | Cohen et al. | 73/862.48 X |
| 3,670,573 | 6/1972 | Kroemer | 73/379 |
| 4,501,148 | 2/1985 | Nicholas et al. | 73/379 |

OTHER PUBLICATIONS

R. A. Dickson et al., "A Device for Measuring the Force of the Digits of the Hand", Bio-Medical Engineering, vol. 7, No. 6, Jul. 1972, pp. 270-273.

J. S. Petrofsky, "Digital Controlled Handgrip for Isometric Performance Studies", N.A.E. Conf., Proceedings IEEE, May 1981, pp. 574-580.

Primary Examiner—Charles A. Ruehl
Attorney, Agent, or Firm—Henry Sternberg; Bert J. Lewen

[57] ABSTRACT

Apparatus (1') for measurement of both the grip strength of a person's hand and pinch strength of two digits of the hand comprises two parallel grip handles (2', 3') extending at right angles from a third member (4'). Handle (3') is rigidly fixed to third member (4') and has two pairs of strain gauges mounted thereon to measure the force applied to the handles irrespective of where that force is applied. Handle (2') is adjustable with respect to handle (3') to alter the distance between the two handles, and the ends of the handles terminate in flat portions (6', 7') to be used for measurement of pinch strength.

7 Claims, 16 Drawing Figures

APPARATUS FOR MEASUREMENT OF GRIP AND PINCH STRENGTH

This is a continuation-in-part of co-pending application Ser. No. 693,178, filed on Jan. 22, 1985, now abandoned.

The present invention relates to apparatus for measuring the grip strength of a person's hand, and also the pinch strength between two digits of the hand.

It is useful for doctors to be able to objectively monitor the progress of patients who have suffered hand injury, either through accidents or debilitating diseases such as arthritis, or who have undergone hand surgery, for example, to replace one of the finger joints with a prosthetic joint.

Several devices exist for measuring grip strength of the hand, but these suffer from several disadvantages.

One such device is described in a paper by Petrofsky et al, "Proceedings of the IEEE 1981 National Aerospace and Electronics Conference, Dayton, Ohio, USA (19th to 21st May 1981)".

This device is designed to measure the grip strength of a pilot's hand, specifically for the purpose of examining isometric performance characterstics. It does not include any means for also measuring the pinch strength between two digits, and would not in any case be suitable for use by a person having fixed flexion deformities resulting from say arthritis, which prevent the person from unclenching their hand completely.

According to the present invention there is provided apparatus for measuring grip strength of a person's hand and pinch strength of two digits of the hand, the apparatus comprising grip handles which are in the form of two substantially parallel elongate members extending substantially at right angles from and attached to a third member, the first of said handles being rigidly fixed to one end of said third member, and the second of said handles being slidably accommodated within said third member so that the distance between the two handles may be altered to adjust the apparatus between a first condition in which it is suitable for measurement of grip strength and a second condition in which it is suitable for measurement of pinch strength, means to lock said second handle in a predetermined position, at least two strain gauges mounted on one or both of the handles to provide an electrical signal indicative of a force applied to the handles, said signal being substantially independent of the point of application of the force, and an electrical connection to a processing and display unit for receiving said signal and converting it to a form suitable for display.

Thus, with the apparatus of the present invention, both the grip strength of a person's hand and the pinch strength of his finger and thumb may be measured using the same piece of apparatus, simply by adjusting the distance between the two handles.

This adjustability also means that if a person has fixed flexion deforminities and is thus unable to clench his hand fully, the distance between the handles can be reduced by sliding the second handle nearer to the first and locking it in position to suit the degree to which the person can unclench his hand.

Preferably the apparatus has four strain gauges mounted in two pairs on the first handle, both members of each pair being connected together in parallel to increase the sensitivity of the apparatus, and each pair being mounted a fixed distance apart along the longitudinal axis of the handle.

Preferably the two pairs of strain gauges are connected into a bridge network, and the processing means calculates the total force applied from the difference between the signals on the two pairs of strain gauges.

This particular arrangement of strain gauges ensures that, within certain limits, wherever the person places his hand or fingers on the handles, the reading obtained from the apparatus will be the same for a given grip or pinch strength. This is particularly desirable when monitoring one person over a long period of time, or when comparing the grip or pinch strength of an arthritic hand with that of a normal one.

Preferably each handle is covered with foam padding and a non-slip material covering on the outside of the padding, such that the part of the handle which is in contact with the person's palm and fingers when used for grip strength measurement, is semi-circular in cross-section and so comfortable to the hand.

Preferably at the end of each handle, furthest away from the third member, there is no padding or covering, and each handle terminates in a flat bare portion suitable for placing a thumb and finger on for measuring pinch strength.

The apparatus may be connected to a simple processor and display means which includes a sample and hold circuit to indicate the highest grip or pinch force in Newton. It may alternatively be connected to a computer which can analyse other aspects of the person's grip or pinch strength, such as grip rate, fatigue rate, fatigue release rate, etc.

The handles may be made of aluminum for persons likely to have a low grip strength of, say, less than 400 Newtons, or alternatively steel handles may be used for use in sports or gymnasium measurements.

Several examples of apparatus in accordance with the invention will now be described with reference to the accompanying drawings, in which FIG. 1 is a schematic view of a first example of the apparatus;

Figure 1:
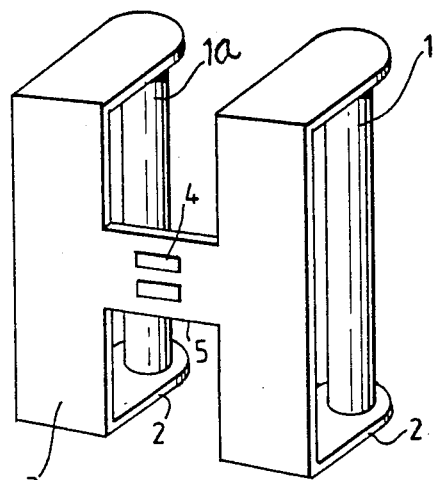
Figure 2:
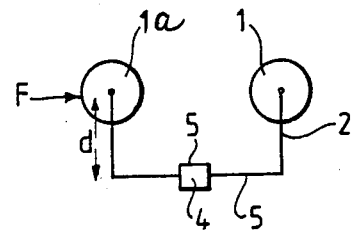
FIG. 2 is a schematic view through the grip measuring apparatus of FIG. 1.

A first example of apparatus in accordance with the invention comprises (see FIG. 1) two parallel grip handles (1, 1a) rotatably mounted on a U-shaped grip member 2. The ends of the U-shape are connected to a perpendicular H-shaped member 3. The grip handles (1, 1a) are rotatably mounted so that any turning forces applied by the grip are eliminated. Members 2 and 3 are made of a metallic material. In the centre bar of the H-shaped member 3 are two strain gauges 4 on one side of the metal and two strain gauges 5 on the opposite side of the metal. When force is applied on the grip handles 1 and 1a force is applied through the two walls of the U-shaped member 2 to the strain gauges 4 to give an electrical signal indicative of the strain applied at this point.

For a force F applied anywhere along the handles 1 or 1a which will always be distance d horizontally from the strain gauges 5 and 4. The force F applied to the member 1 will be proportional to $F \times d$. As d is constant the strain measured by the strain gauges 4 and 5 will be directly proportional to F.

The two sets of strain gauges at 5 are required to correct the temperature which has an effect on the readings of the strain gauges. Each strain gauge is a transducer which has a resistance which varies according to the strain applied to the transducer.

Figure 3:
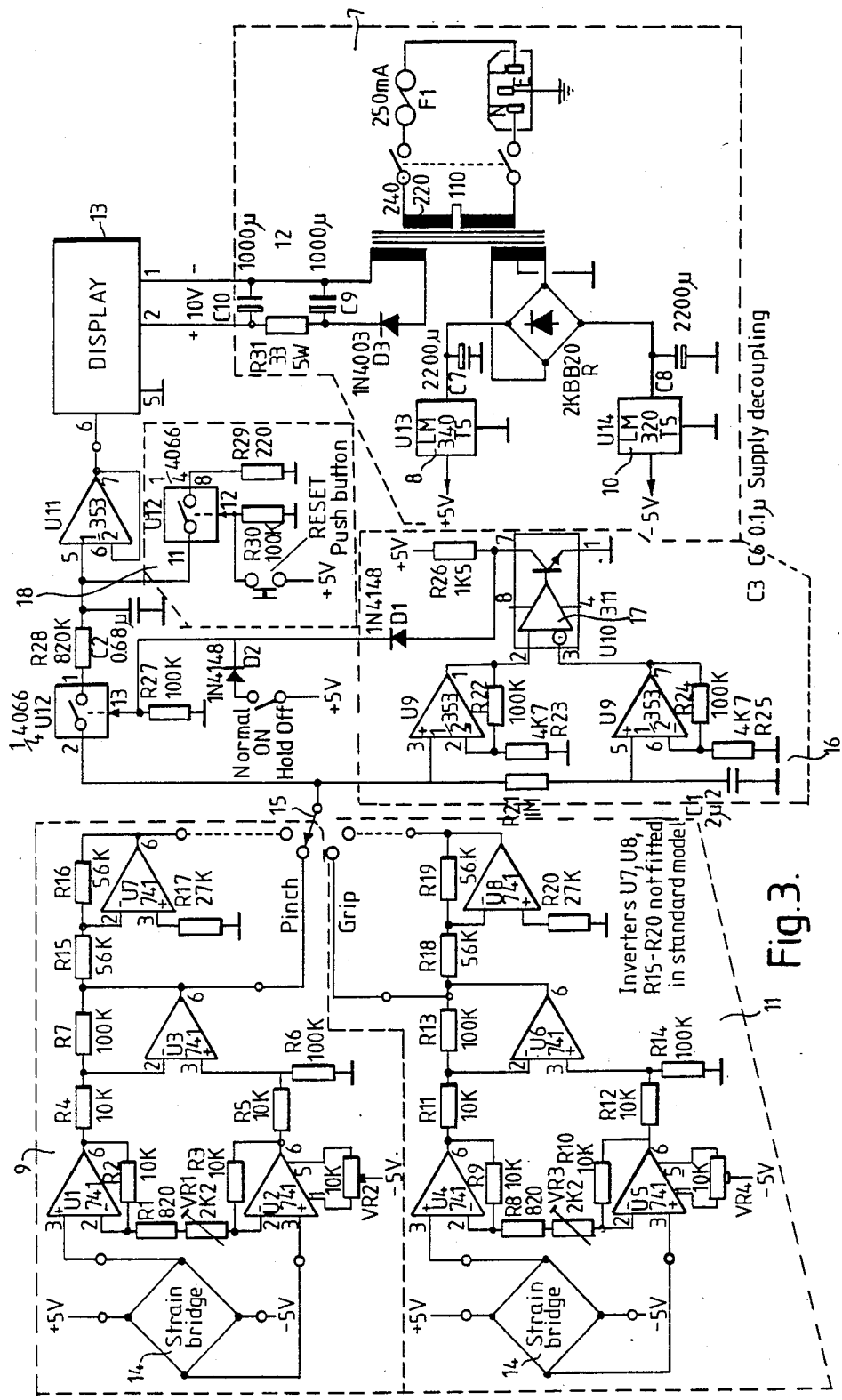
FIG. 3 is a circuit diagram of the processor means.
Figure 8:
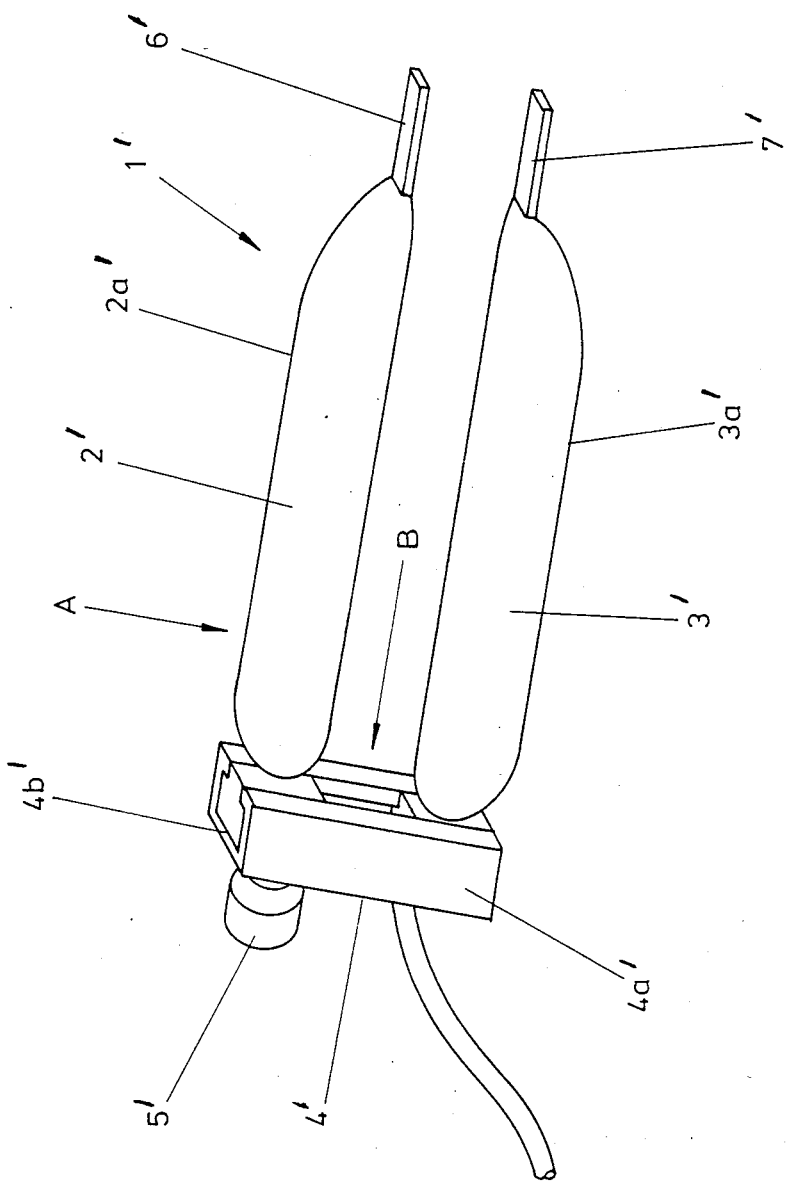
FIG. 8 is a perspective view of the apparatus of the present invention.
Figure 9:
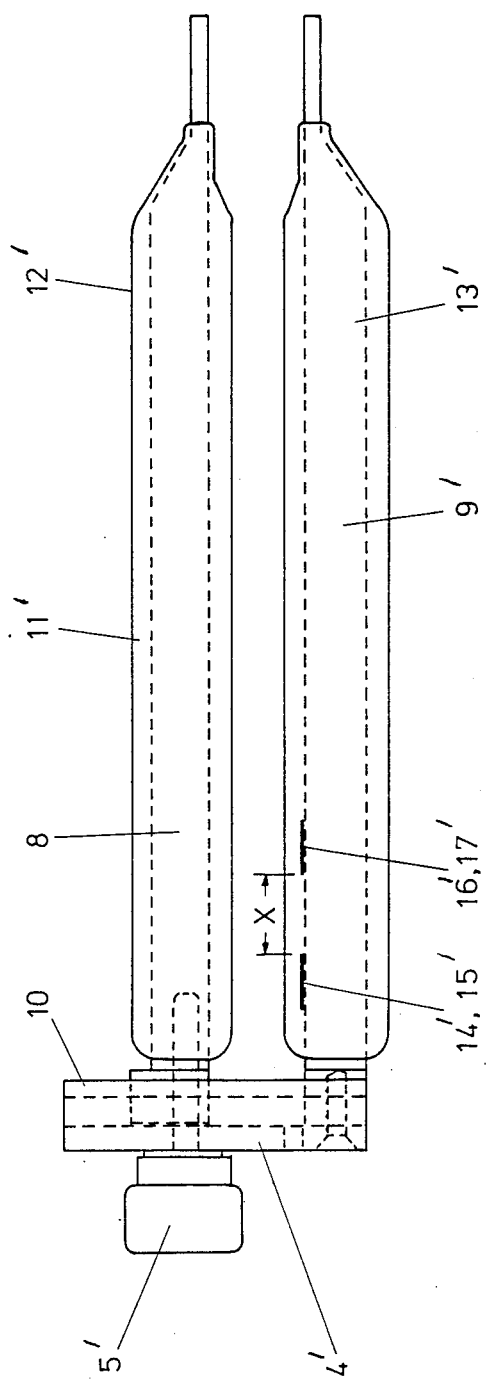
FIG. 9 is a side view, showing internal detail of the apparatus of the present invention.
Figure 10:
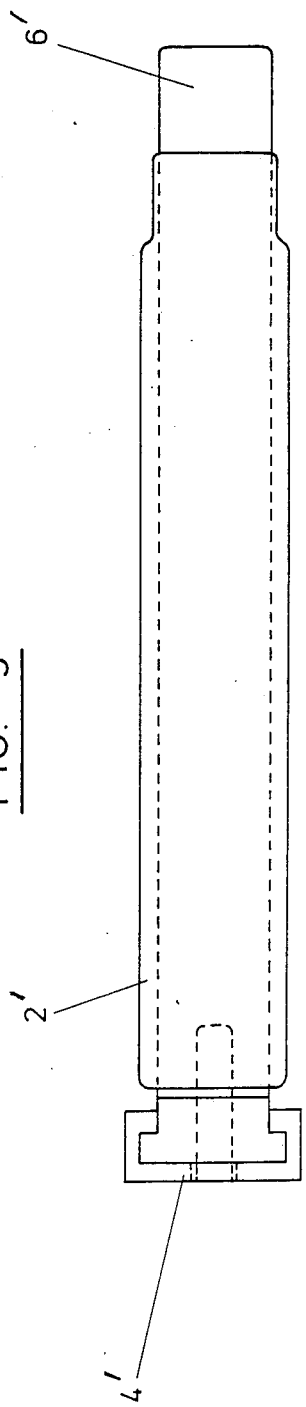
FIG. 10 is a top plan view in the direction A of the apparatus shown in FIGS. 8 and 9, showing details of the second handle.
Figure 11:
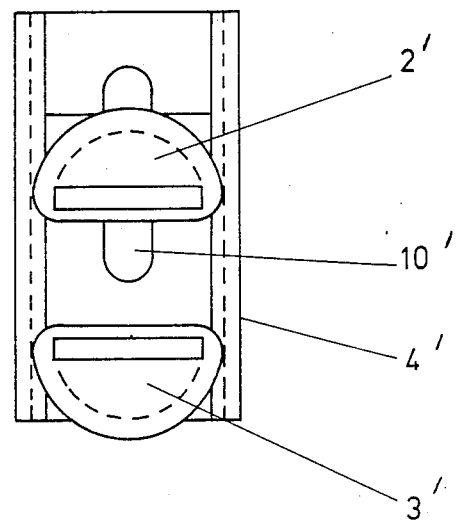
FIG. 11 is a plan view in the direction B of the apparatus shown in FIGS. 8, 9 and 10.

The signal from the strain gauge are fed to the processor unit 6 shown in detail in FIG. 3. The processor includes a power supply circuit 7 which provides three separate supplies. A first supply 8 supplies the pinch amplification circuit 9 and the second supply 10 supplies the grip amplification circuit 11 and the third supply 12 supplies the display circuits 13. The pinch amplification circuit 9 and the grip amplification circuit 11 comprise a strain bridge 14 which is a Wheatstone bridge of the transducers forming the strain gauges (4, 5) and amplifiers to amplify the resultant signals. The power supplies 8 and 10 are on constantly so that the transducers forming the strain gauges are always on. This is advantageous since the transducers require to be warmed up and so there is no warming up period required. A switch 15 switches the signals according to whether the pinch of the digits of the hand is to be measured or whether the grip of the hand is to be measured. A logic circuit 16 is used to store the value of the signal fed through switch 15. Since logic gates 17 are used the signal can be stored for up to 20 seconds which is much longer than would be possible if capacitors were used. A sample and hold circuit 18 tests the signal to find whether it is higher than that stored in the logic gates 17. If it is the new value replaces the value in the logic circuit 16. The display may be used on a logic circuit 16. The display may be also used on a normal mode which just displays the instantaneous value coming through switch 15.

Figure 4:
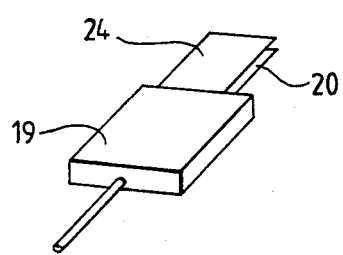
FIG. 4 is a perspective view of the pinch meter of the first example of the appratus.
Figure 5:
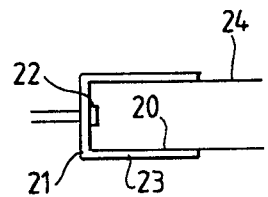
FIG. 5 is a section through the pinch meter of FIG. 4.
Figure 6:
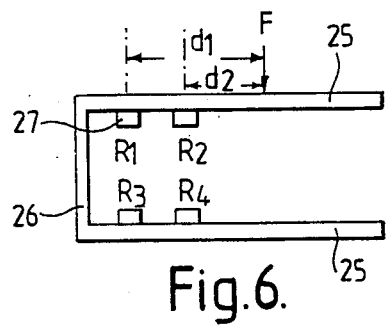
FIG. 6 is a schematic view of a second example of apparatus.
Figure 7:
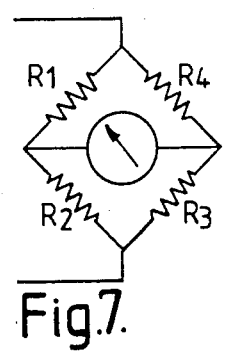
FIG. 7 is a view of the circuit arrangement used in the processor of the apparatus of FIG. 6.

The pinch meter is shown schematically in FIGS. 4 and 5. The meter 19 comprises a bifurcated member 20 with two parallel members joined together at one end 21. Strain gauges 22 are situated at end 21 to measure the strain produced by movement of members 20, a plastic guard 23 is placed over the bifurcated member 20 to limit the surfaces 24 which can be used by the operator to pinch the members 20 together. These readings are then fed to the pinch amplification circuit 9 of the processor unit.

A second example of the apparatus obviates the requirement for a pinch meter 19 and comprises two substantially parallel handles 25 connected together at one end 26. Each member 25 has two transducers or strain gauges 27 near end 26. For a force applied F at a distance $d_1$ from first transducer $R_1$, and $d_2$ from the second transducer $R_2$, the difference between the two signals of the transducers $R_1$ and $R_2$ will be $F \times d_1 - F \times d_2$ which will equal $F \times X$ where X is the distance between the two transducers which is constant. This means that for a given force applied the same electrical signal will be produced by the transducers wherever the force is applied.

This can be conveniently achieved by producing a Wheatstone bridge of the outputs of the transducers $R_1$, $R_2$, $R_3$ and $R_4$, to provide an electrical signal indicative of the force applied on the two members 25.

Referring to FIGS. 8, 9, 10 and 11 of the accompanying drawings, apparatus according to the present invention comprises two handles 2', 3' in the form of elongate members 8', 9'. The elongate members 8', 9' are attached to and extend at right angles from a third, U-shaped member 4'.

One of the handles, 3', is rigidly fixed at end 4A' of the U-shaped member 4', and the other handle, 2', is slidably secured within the U-shaped member 4' and includes a locking knob 5' which is used to lock the handle 2' into a predetermined position relative to the handle 3'. The U-shaped member 4' has a slot 10' within which the handle 2' can slide.

Each handle comprises a metal body 13', surrounded by foam padding 11' and a plastic non-slip cover 12'. The padding is such that the surface of the handles in contact with the person's palm and fingers is semi-circular in shape, and so is comfortable to the hand.

Two pairs of strain gauges 14', 15' and 16', 17' are mounted on the inside of metal body 13'. Gauges 14' and 15' are wired in parallel, as are gauges 16' and 17', and the two pairs are connected into a bridge network located in the processing unit. Pair 16', 17' is offset from pair 14', 15' by a distance X along the longitudinal axis of the handle 3'. The use of two pairs of strain gauges in this way increases the sensitivity of the apparatus.

Each handle 2', 3' has at its tip a flat, bare metal portion 6', 7' so that the same apparatus may be used for both the measurement of pinch strength and grip strength, by adjusting the distance between the handles 2', 3'.

Figure 12:
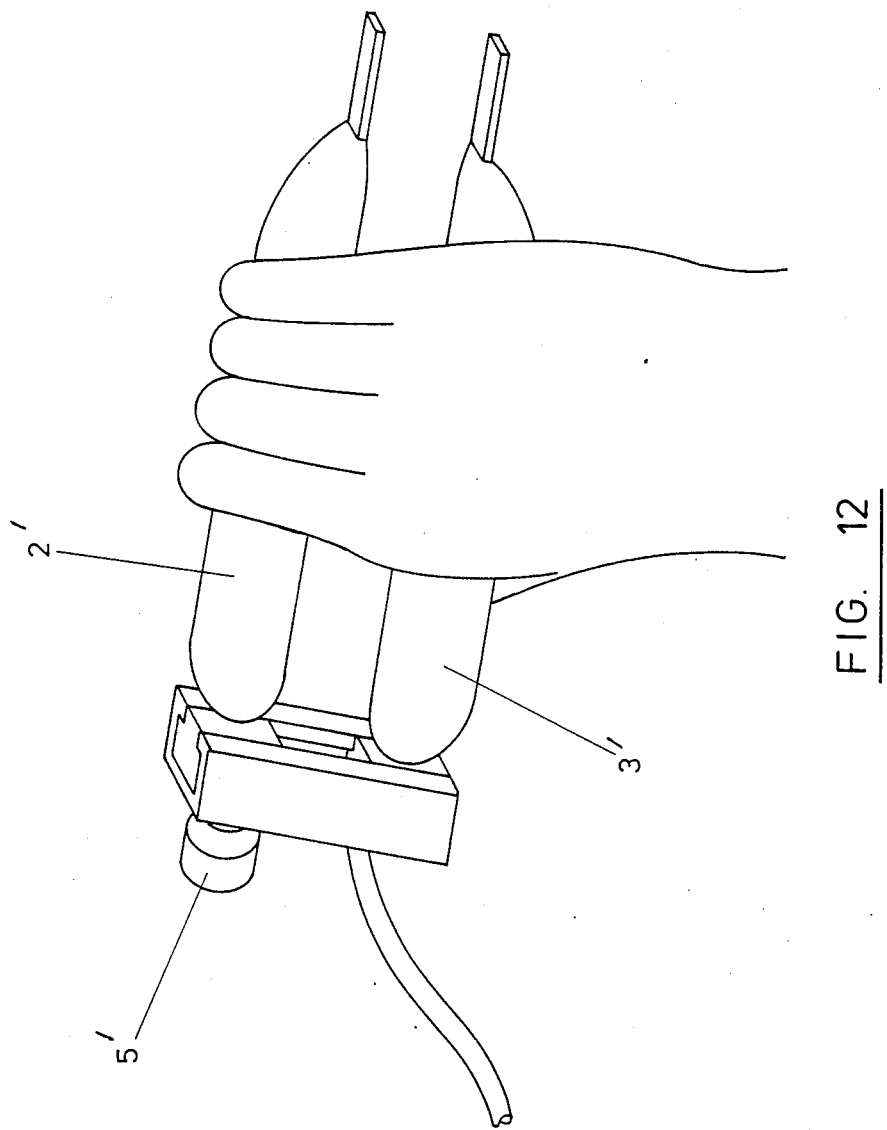
FIG. 12 shows the apparatus of the present invention being used for the measurement of grip strength.

Referring now to FIG. 12, when the apparatus is to be used for measurement of grip strength, the knob 5' is released, and the handle 2' is slid to a suitable position to suit the person's hand, the knob 5' is then tightened, and the person places his thumb around the handle 3' and all his fingers around handle 2' and squeezes as hard as he can.

Figure 13:
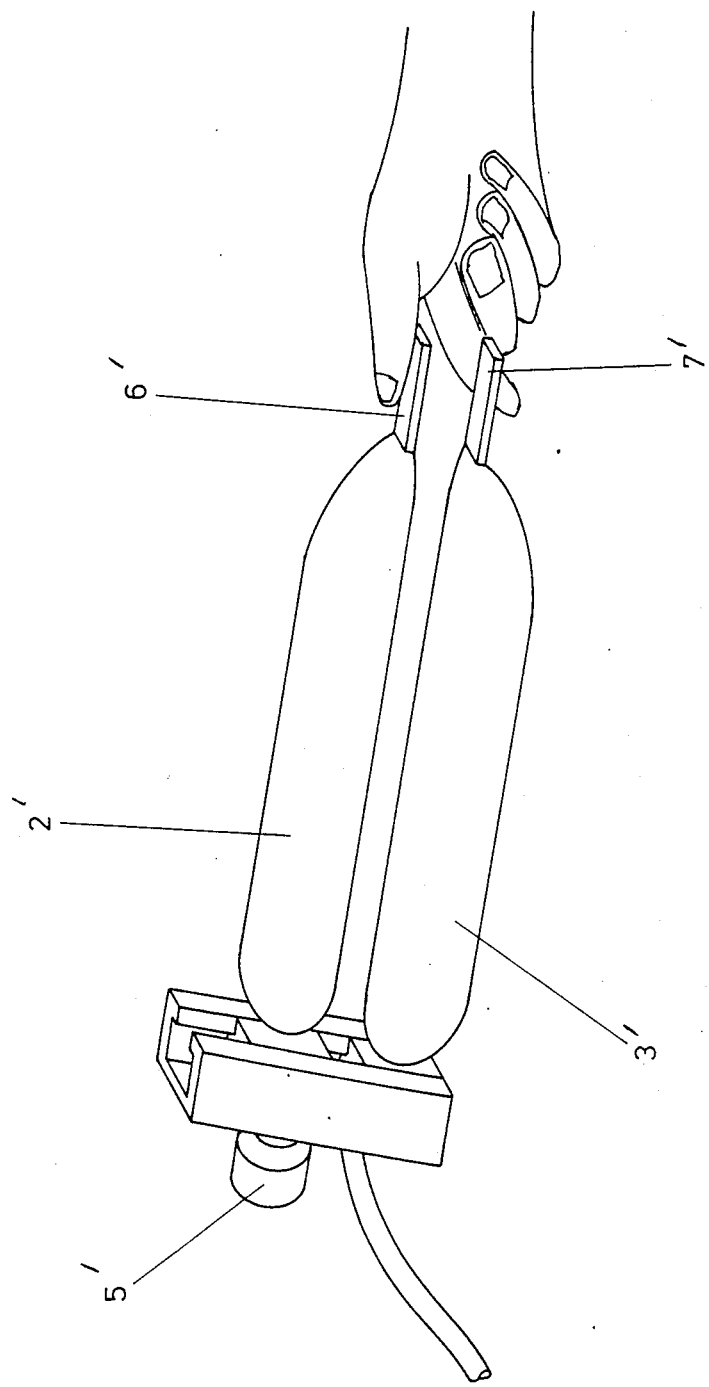
FIG. 13 shows the apparatus of the present invention being used for the measurement of pinch strength.

Referring to FIG. 13, to adjust the apparatus for measuring pinch strength, the knob 5' is released, the handle 2' is slid down unti it is close to handle 3' the person places a finger under portion 7' and a thumb on top of portion 6' and pinches the two together as hard as he can.

Figure 16:
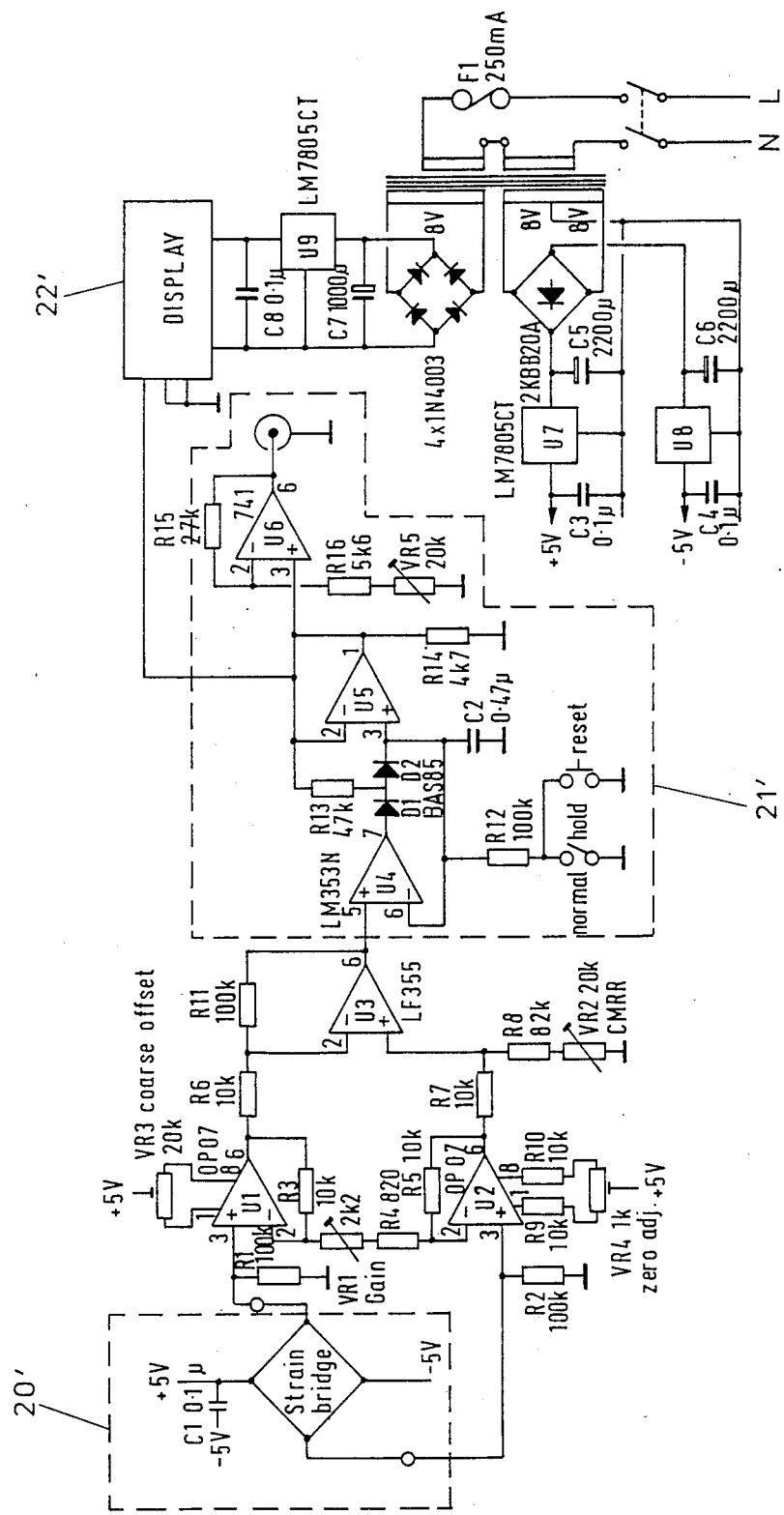

Referring now to FIG. 16, the processing means to which the apparatus is connected measures the difference between the signals produced at each pair of strain gauges as measured by a bridge network 20'. This difference, which is indicative of the force applied regardless of the point of application of the force, is amplified and then fed to sample and hold circuitry 21' and thereafter to a display unit 22'. The sample and hold circuitry stores the highest difference measured, so that a person may have several attempts at using the apparatus, and only the highest force will be displayed.

Since it is the difference between the signals at the two pairs of strain gauges which is measured, the reading displayed is independent of the point of application of the force.

This is substantiated by results of tests on two different types of metal, using standard weights of 10 Kg and 20 Kg applied at different points along the handles, instead of a person's grip.

Figure 14:
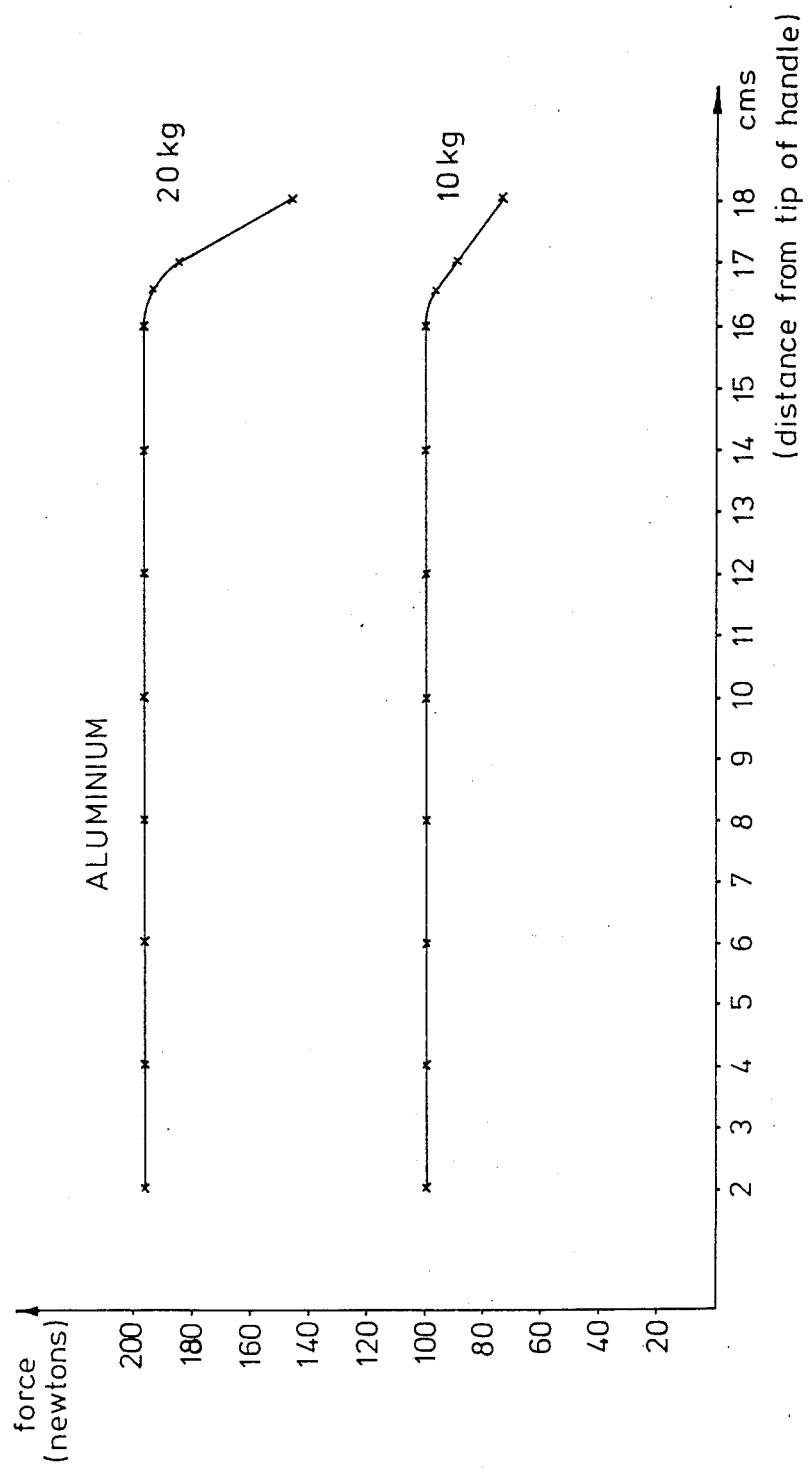
FIG. 14 shows displayed force plotted as a function of distance of point of application of force from the tip of the handle, for two different constant forces and aluminium handles.

FIG. 14 shows the results for aluminium handles, and it can be seen from this graph that there is very little variation for each weight up to a distance of 16 cm from the tip of the handle.

Figure 15:
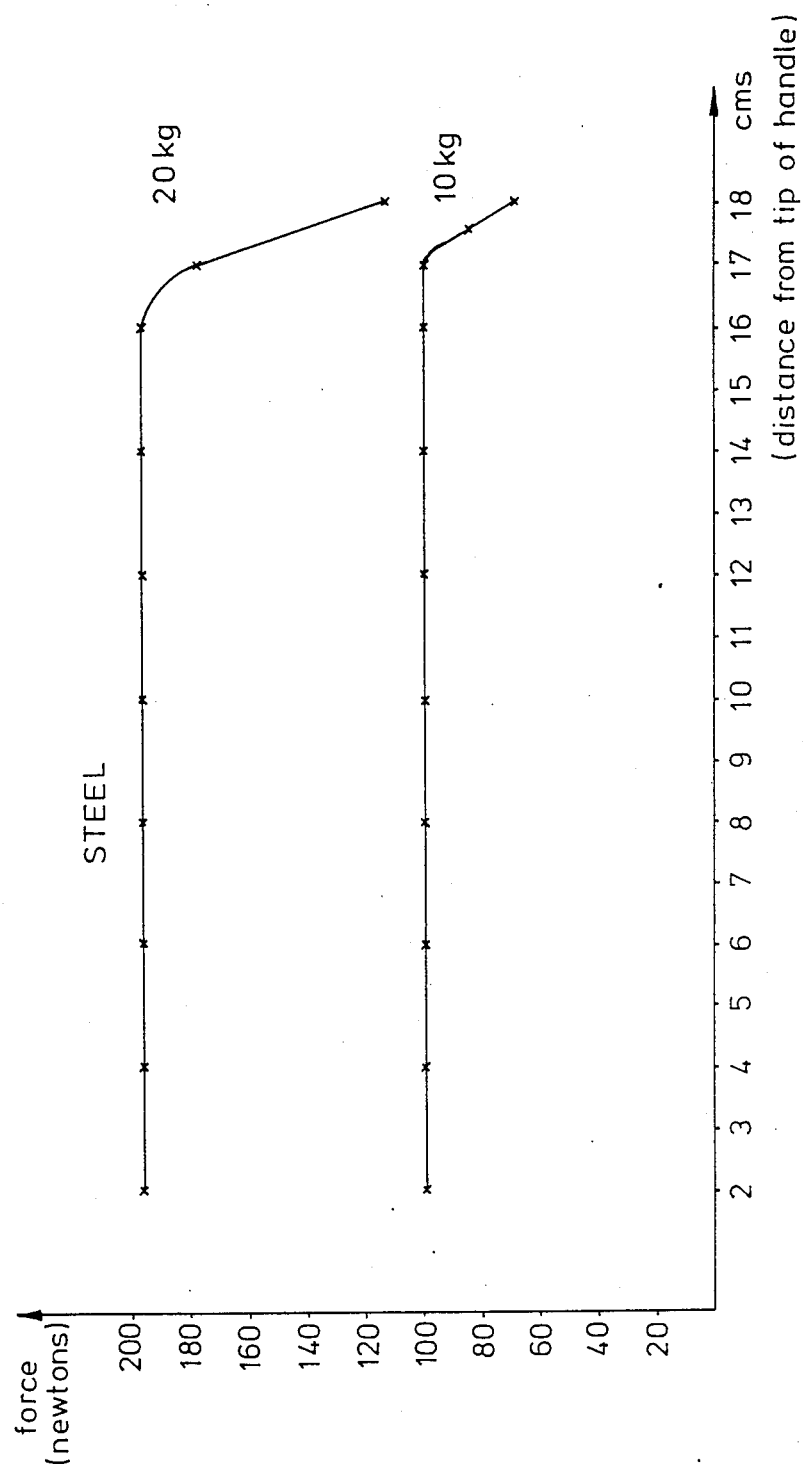
FIG. 15 shows displayed force plotted as a function of distance of point of application of force from the tip of the handle, for two different constance forces and steel handles; and, FIG. 16 is a circuit diagram of a processor and display unit for use with the apparatus of the present invention.

Similarly, FIG. 15 shows the results of the same test carried out on steel handls, and this also shows very little variation between different points of application of the force, up to 17 cm from the tip of the handle in the case of 10 Kg, and 16 cm in the case of 20 Kg.

I claim:

1. Apparatus for measuring grip strength of a person's hand and pinch strength of two digits of the hand, the apparatus comprising grip handles which are in the form of two substantially parallel elongate members extending substantially at right angles from and attached to a third member, the first of said handles being rigidly fixed to one end of said third member, and the second of said handles being slidably accommodated within said third member so that the distance between the two handles may be altered to adjust the apparatus between a first condition in which it is suitable for measurement of grip strength and a second condition in which it is suitable for measurement of pinch strength, means to lock said second handle in a predetermined position, at least two strain gauges mounted on one or both of the handles to provide an electrical signal indicative of a force applied to the handles, said signal being substantially independent of the point of application of the force, and an electrical connection to a processing and display unit for receiving said signal and converting it to a form suitable for display.

2. Apparatus according to claim 1 in which four strain gauges are mounted in two pairs on the first handle, both members of each pair being connected together in parallel to increase the sensitivity of the apparatus, and each pair being mounted a fixed distance apart along the longitudinal axis of the handle.

3. Apparatus according to claim 2 in which the two pairs of strain gauges are connected into a bridge network, and the processing means calculates the total force applied from the difference between the signals on the two pairs of strain gauges.

4. Apparatus according to claim 2 in which the handles are made of steel.

5. Apparatus according to claim 1 in which each handle is covered with foam padding and a non-slip material covering on the outside of the padding.

6. Apparatus according to claim 5 in which, at the end of each handle furthest away from the third member there is no padding or covering, each handle terminating in a flat bare portion suitable for placing a thumb and finger on for measuring pinch strength.

7. Apparatus according to claim 1 in which the handles are made of aluminium.

* * * * *